(12) United States Patent
Kuo

(10) Patent No.: US 11,938,485 B2
(45) Date of Patent: Mar. 26, 2024

(54) HEATING DEVICE FOR CONVECTIVE POLYMERASE CHAIN REACTION

(71) Applicant: Industrial Technology Research Institute, Hsinchu (TW)

(72) Inventor: Chien-Chih Kuo, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 83 days.

(21) Appl. No.: 17/544,301

(22) Filed: Dec. 7, 2021

(65) Prior Publication Data

US 2023/0173496 A1 Jun. 8, 2023

(51) Int. Cl.
| | |
|---|---|
| *C12Q 1/686* | (2018.01) |
| *B01L 7/00* | (2006.01) |
| *F25B 49/00* | (2006.01) |
| *F25B 30/00* | (2006.01) |

(52) U.S. Cl.
CPC ............ *B01L 7/52* (2013.01); *B01L 7/54* (2013.01); *C12Q 1/686* (2013.01); *F25B 49/00* (2013.01); *B01L 2200/147* (2013.01); *B01L 2300/1822* (2013.01); *F25B 30/00* (2013.01)

(58) Field of Classification Search
CPC ........ B01L 7/52; B01L 7/54; B01L 2200/147; B01L 2300/1822; C12Q 1/686
See application file for complete search history.

(56) References Cited

U.S. PATENT DOCUMENTS

| | | |
|---|---|---|
| 6,402,369 B1 | 6/2002 | Ludington et al. |
| 7,578,976 B1 | 8/2009 | Northrup et al. |
| 9,126,201 B2 | 9/2015 | Chen et al. |
| (Continued) | | |

FOREIGN PATENT DOCUMENTS

| | | |
|---|---|---|
| CN | 106244447 A | 12/2016 |
| CN | 109957494 B | 5/2020 |
| (Continued) | | |

OTHER PUBLICATIONS

Pathak et al., "Heat Pump Design Using Peltier Element for Temperature Control of the Flow Cell," IJCSEA, June, vol. 3, No. 3, pp. 41-47. (Year: 2013).*

(Continued)

*Primary Examiner* — Young J Kim
(74) *Attorney, Agent, or Firm* — WPAT, P.C

(57) ABSTRACT

A heating device includes a heating element, a temperature sensor, a first heat pump element, a first heating block, a second heating block and a controller. The heating element is to receive an energy of the controller and convert the energy into a first thermal energy provided to the first heating block. A sensing result is generated by the temperature sensor according to the first thermal energy. The first heat pump element is to receive the energy of the controller for generating a temperature difference. The first thermal energy is conducted to the first heat pump element for forming a second thermal energy. The second heating block is to receive the second thermal energy. The controller correspondingly outputs the energy to the heating element (Continued)

and the first heat pump element according to the sensing result, and thereby controls the first thermal energy and the temperature difference.

16 Claims, 17 Drawing Sheets

(56) References Cited

U.S. PATENT DOCUMENTS

| | | | |
|---|---|---|---|
| 9,357,764 | B2 | 6/2016 | Tempelman et al. |
| 9,731,296 | B2 | 8/2017 | Su et al. |
| 9,765,376 | B2 | 9/2017 | Hwang et al. |
| 10,086,374 | B2 | 10/2018 | Hwang |
| 10,086,375 | B2 | 10/2018 | Hwang |
| 2009/0020429 | A1* | 1/2009 | Ozawa ............. G01N 27/44708 204/604 |

FOREIGN PATENT DOCUMENTS

| | | |
|---|---|---|
| JP | 2009171868 A | 8/2009 |
| JP | 2011-188749 A | 9/2011 |
| JP | 2013198409 A | 10/2013 |
| JP | 2014100145 A | 6/2014 |
| JP | 2016144479 A | 8/2016 |
| JP | 2018-29514 A | 3/2018 |
| TW | I427143 | 2/2014 |
| TW | I445819 | 7/2014 |
| TW | I482856 | 5/2015 |
| TW | I539001 | 6/2016 |
| TW | I561308 | 12/2016 |
| TW | 201809284 A | 3/2018 |
| TW | I656211 | 4/2019 |
| WO | WO-2012038750 A1 * | 3/2012 ............. B01J 19/24 |

OTHER PUBLICATIONS

Priye et al. "Education: DNA replication usingmicroscale natural convection", 2012, Lap Chip, The Royal Society of Chemistry.
Krishnan et al. "PCR in a Rayleigh-Benard ConvectionCell", 2002, vol. 298, www.sciencemag.org.
Rajendran et al. "Smartphone detection of antibioticresistance using convective PCR and alateral flow assay", 2019, Sensors and Actuators B: Chemical, Elsevier.
Rajendran et al. "A portable nucleic acid detection systemusing natural convection combined witha smartphone", 2019, Biosensors and Bioelectronics, Elsevier.
Chou et al. "Development of Capillary Loop Convective Polymerase Chain Reaction Platform with Real-Time Fluorescence Detection", 2017, www.mdpi.com/journal/inventions.
Braun et al. "Exponential DNA Replication by Laminar Convection", 2003, Physical Review Letter, The American Physical Society.
Agrawal et al. "A Buoyancy-Driven Compact Thermocycler for Rapid PCR" 2006, Technical Brief, SAGE Publication.
Qiu et al. "A Low-Cost and Fast Real-Time PCRSystem Based on Capillary Convection", 2016, Technology Brief, SLAS Technology.
Ge et al. "Free Convective PCR: From Principle Study to Commercial Applications—A Critical Review", 2020, Analytica Chimica Acta, Elsevier.
Ajit et al. "Towards rapid prototyped convective microfluidic DNA amplification platform", 2017, SPIE BiOS, San Francisco, USA.
TW OA issued on Aug. 11, 2022.
JP NOA issued on Mar. 7, 2023.

* cited by examiner

HEATING DEVICE FOR CONVECTIVE POLYMERASE CHAIN REACTION

TECHNICAL FIELD

The present disclosure relates in general to a heating device for a convective polymerase chain reaction, and more particularly to the heating device for a convective polymerase chain reaction that is provided with a heat pump element.

BACKGROUND

With the prevalence of various infectious diseases, rapid and accurate virus detection methods are urgently needed to prevent and monitor possible pandemics.

In the traditional convective polymerase chain reaction, a container containing samples to be tested would be directly heated in a convection manner so as to form a temperature gradient at each of the samples. Upon such a convective heating, the samples would vary their own temperatures up and down repeatedly, and thus expected heat circulation would be induced to perform the nucleic acid amplification.

In order to generate the temperature gradient for inducing the heat convection at each of the samples, two heating blocks with different temperatures would be set at opposite ends of the container, and each of the two heating blocks would be furnished with a heating element and a temperature sensor for controlling temperatures. To construct the heating device, structural fixings are required to fix the two heating blocks. In this way, the constructed heating device can be used to heat the container and form internal heat convections.

However, there are many problems with the aforesaid design. For example, if one of the two heating blocks generates a 60° C. and another thereof generates a 95° C., then, according to the basic thermodynamic theory that the thermal energy would flow from the high-temperature end to the low-temperature end, the low temperature zone would be susceptible to thermal disturbances from the high temperature zone, caused by heat conduction at the structural fixings. Thereupon, it is quite possible that an abnormality in temperature control would be formed in the low temperature zone. An improvement method is introduced anyway to change materials of the structural fixings of the two heating blocks into high thermal resistance materials, and so the conduction speed of thermal energy would be slowed down so as to lessen effectively the aforesaid phenomenon. Although this method improves the problem of thermal disturbances to some degree in the heating stage, yet another problem would be formed that the temperature conduction rate in the heat dissipation stage would be too slow to effectively dissipate the heat. To resolve this shortcoming practically, specific active components such as fans shall be introduced to improve the heat dissipation efficiency in the heat dissipation stage, but a larger overall volume and higher cost would be inevitable.

In another effort, the original heating element on the heating block is replaced by a heat pump element. The heat pump element can form a temperature difference ($\Delta T$) between cold and hot surfaces, but the aforesaid heating element generates a uniform temperature (T). In application, this structure shall provide a stable reference temperature to either the cold surface or the hot surface, and this reference temperature is usually equal to the ambient temperature. For example, in order to make the temperature of a heating block reach 60° C., the easiest way is to generate a temperature of 60° C. on the hot surface of the heat pump element, and then install a heat sink with a fan on the cold surface of the same heat pump element. Assuming the current environment temperature is 25° C. which will be assigned to the cold surface, then the temperature difference ($\Delta T$) of the heat pump element would be 60° C.−25° C.=35° C. With this temperature difference ($\Delta T$) for the heating block, then the desired 60° C. temperature can be reached. If the temperature of another heating block is expected to reach 95° C., then a temperature of 95° C. would be generated on the hot surface of this heat pump element, and also a heat sink and a fan would be installed on the cold surface of the heat pump element to reach thereon the ambient temperature (25° C.). That is, the temperature difference ($\Delta T$) of the corresponding heat pump element, 95° C.−25° C.=70° C., can drive the temperature of the heating block to reach 95° C.

Nevertheless, a limit of the foregoing design is that the maximum operating temperature difference of the current heat pump element is about 80° C., and thus the 70° C. temperature difference calculated above is close to the upper limit. Hence, if the operating environment is located at an area with a higher latitude or a higher altitude or facing a cold front, whose room temperature usually drops below 15°, then this design will not work properly there. Further, to operate constantly under the extreme conditions, a negative impact on the service life of the heat pump element can be expected. In addition, if the operating temperature difference of the heat pump element is too large, then the energy efficiency thereof would be worse, and an increase in the power consumption of this design would be inevitable.

Therefore, there is a need to provide a heating device for a convective polymerase chain reaction that can relieve the aforesaid concerns.

SUMMARY

An object of the present disclosure is to provide a heating device for a convective polymerase chain reaction.

In one embodiment of this disclosure, a heating device for a convective polymerase chain reaction, applied to form a temperature gradient and heat convection to a container, includes: a heating element, configured to receive an energy and further transform the energy into a first thermal energy; a temperature sensor, configured to generate a sensing result according to the first thermal energy; a first heat pump element, having a first surface and a second surface, configured to receive the energy and further generate a first temperature difference between the first surface and the second surface; a first heating block, contacted with the first surface of the first heat pump element and also the heating element, configured to receive the first thermal energy from the heating element and further transfer the first thermal energy to the first heat pump element, so as to have the first heat pump element to utilize the first thermal energy and the first temperature difference to generate a second thermal energy; a second heating block, contacted with the second surface of the first heat pump element, configured to receive the second thermal energy of the first heat pump element; and, a controller, electrically connected with the temperature sensor, the heating element and the first heat pump element, configured to output the energy in correspondence with the sensing result of the temperature sensor to the heating element and the first heat pump element, so as to control the first thermal energy of the heating element and the first temperature difference of the first heat pump element.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

In this disclosure, a heating device for a convective polymerase chain reaction is provided to generate temperature gradients inside a bio-reaction chamber, by which heat convections can be formed thereinside to promote nucleic acid amplification. In order to explain more concisely the structures, the objects, the features and the merits of this disclosure, plural embodiments accompanied by schematic drawings will be used in the description as follows.

In the following detailed description, these embodiments are particularly shown and described to illustrate technical features of the subject matter set forth in this disclosure, not used to limit the claims of this disclosure. To any normal skilled in the art after he or she understands the teaching of this disclosure, any equivalent modification or variation therefrom is deemed not to exceed or depart from the spirit and scope of this disclosure.

Figure 1A:
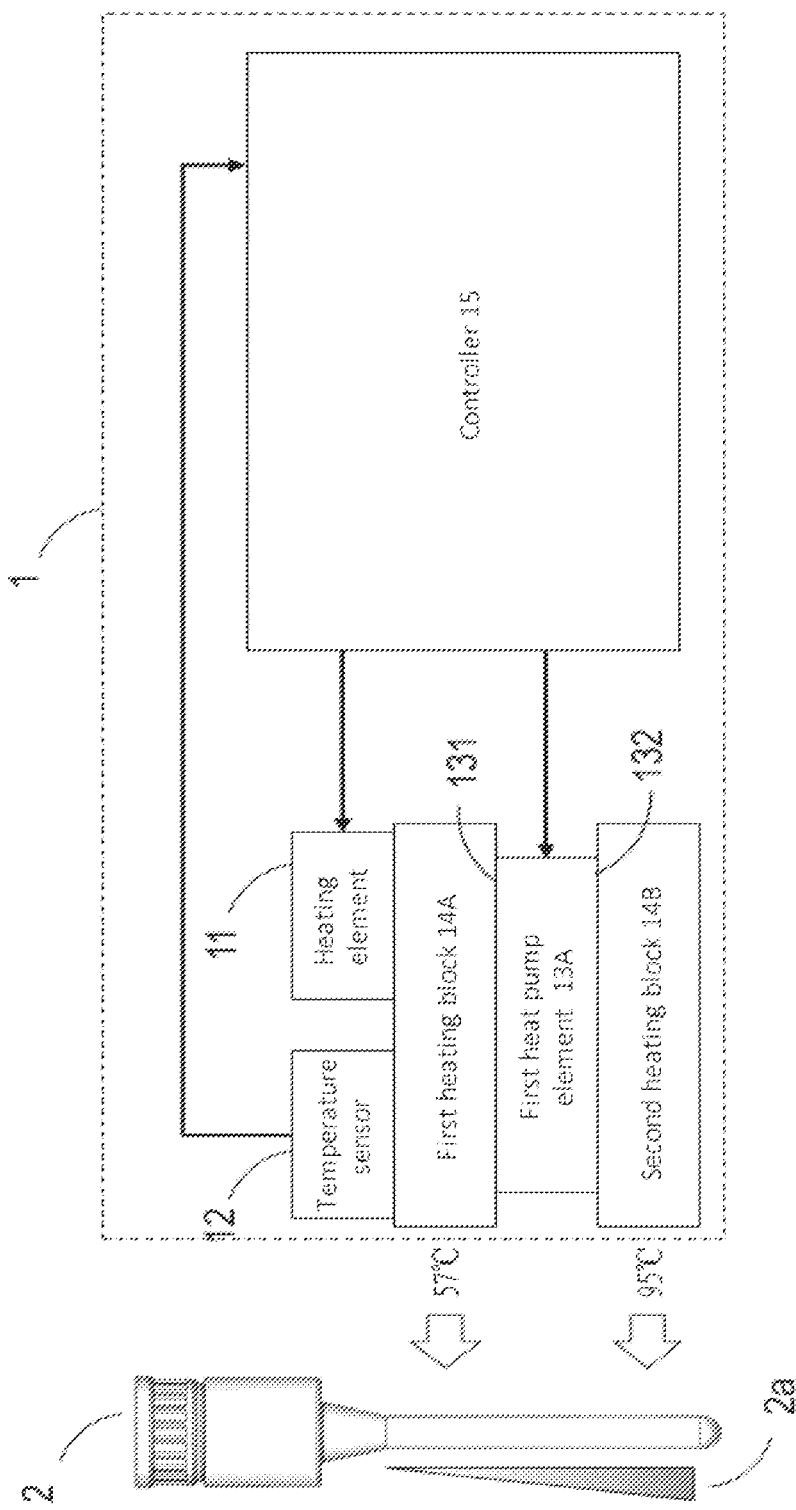
FIG. 1A is a schematic view of a first embodiment of the heating device for a convective polymerase chain reaction in accordance with this disclosure.
Figure 1B:
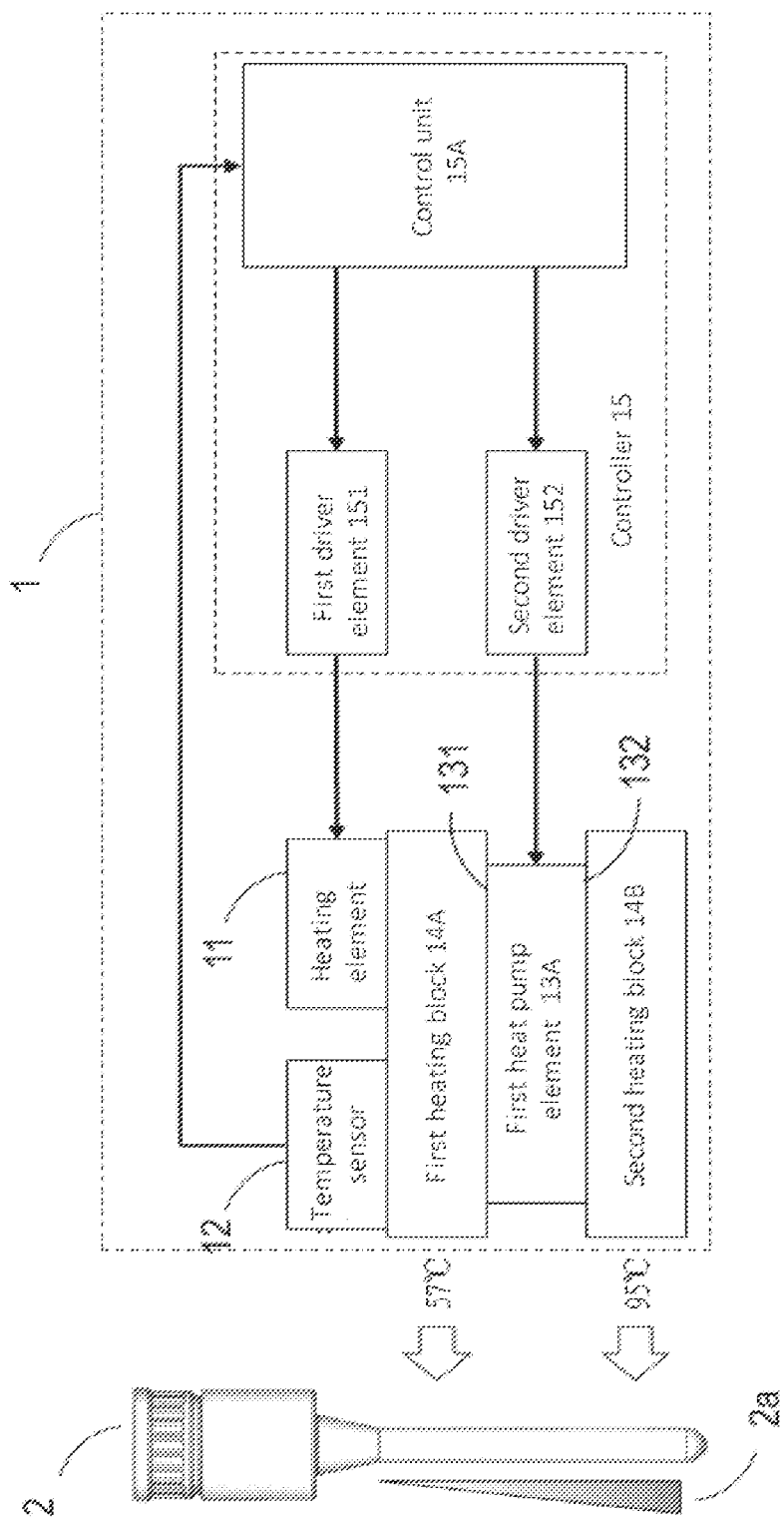
FIG. 1B shows schematically FIG. 1A with an exemplary example of the controller in detail.

Refer to FIG. 1A and FIG. 1B; where FIG. 1A is a schematic view of a first embodiment of the heating device for a convective polymerase chain reaction in accordance with this disclosure, and FIG. 1B shows schematically FIG. 1A with an exemplary example of the controller in detail. As shown, the heating device for a convective polymerase chain reaction 1 is a device that can form a temperature gradient 2a to induce heat convection inside a container 2. In this embodiment, the container 2 can be a bio-reactor having a pipe to carry thereinside the temperature gradient 2a formulated by the heating device for a convective polymerase chain reaction 1. In the drawing, the color of the temperature gradient 2a varies from a light color to a dark color, and it implies, but not limited thereto, that the temperature varies from a low temperature to a high temperature, respectively. Thereupon, the temperature gradient 2a would induce heat convection and heat circulation for performing nucleic acid amplification in the container 2. The heating device for a convective polymerase chain reaction 1 includes a heating element 11, a temperature sensor 12, a first heat pump element 13A, a first heating block 14A, a second heating block 14B and a controller 15.

The heating element 11 is configured to receive an energy of the controller 15 and then transform the energy into a first thermal energy, in which the energy can be transmitted in an electric waveform, but not limited thereto. The heating element 11 can be a resistance heater, a thin film heater, a PTC heater, etc.; but not limited thereto.

The temperature sensor 12 can evaluate the first thermal energy to further generate a sensing result, in which the temperature sensor of this embodiment can be a thermocouple, a thermistor, a temperature sensing IC, etc.; but not limited thereto.

Figure 1C:
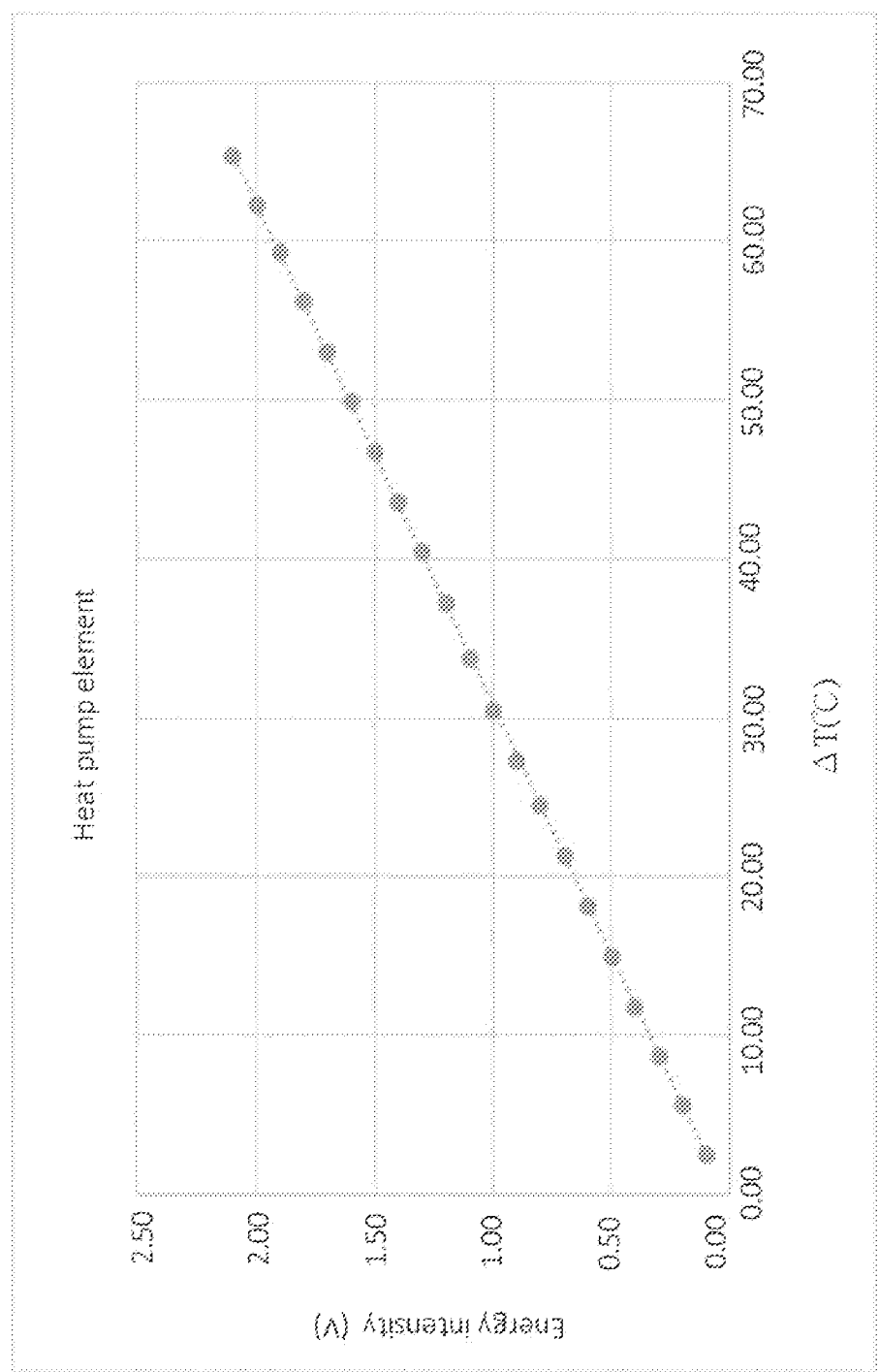
FIG. 1C demonstrates schematically a relationship between the temperature difference and the energy intensity for the heat pump element (temperature-energy relationship, hereinafter) in accordance with this disclosure.

The first heat pump element 13A, having a first surface 131 and a second surface 132, is configured to receive the energy of the controller 15, and further to generate a first temperature difference between the first surface 131 and the second surface 132. In this embodiment, the energy required to produce the first temperature difference can be obtained through a temperature-energy relationship (for example, a linear equation or a lookup table). Regarding the aforesaid temperature-energy relationship, please refer to FIG. 1C, where a temperature-energy relationship for the heat pump element is shown. In FIG. 1C, the temperature difference ΔT (° C.) stands for the temperature difference between the first surface 131 and the second surface 132. Based on the required temperature difference, the controller 15 would determine the energy output (voltage) to the first heat pump element 13A in accordance with the temperature-energy relationship. In some exemplary examples, the first heat pump element 13A can be a Peltier element, but not limited thereto.

The first heating block 14A is disposed by contacting both the first surface 131 of the first heat pump element 13A and the heating element 11, and configured to receive the first thermal energy of the heating element 11 and further transfer this energy to the first heat pump element 13A, such that the first heat pump element 13A can evaluate the first thermal energy and the first temperature difference to form a second thermal energy. The second heating block 14B, contacted with the second surface 132 of the first heat pump element 13A, is configured to receive the second thermal energy of the first heat pump element 13A. In this embodiment, each of the first heating block 14A and the second heating block 14B is made of a low thermal resistance material, such as aluminum, copper, ceramic, etc.; but not limited thereto.

In this embodiment, the first heat pump element 13A is disposed between the first heating block 14A and the second heating block 14B. In addition, the temperature sensor 12 is disposed to contact the first heating block 14A. According to the first thermal energy of the first heating block 14A, the sensing result is sent back to the controller 15 for further calculation, such that the controller 15 can control the energy output to the heating element 11.

The controller 15, electrically connected with the temperature sensor 12, the heating element 11 and the first heat pump element 13A, would evaluate the sensing result of the temperature sensor 12 and the required first temperature difference to output corresponding energies to the heating element 11 and the first heat pump element 13A, such that the first thermal energy of the heating element 11 and the first temperature difference of the first heat pump element 13A can be controlled. In this embodiment, the controller 15 further includes a first driver element 151, a second driver element 152 and a control unit 15A. The first driver element 151, electrically connected with the heating element 11, is configured to output an energy to the heating element 11. The second driver element 152, electrically connected with the first heat pump element 13A, is configured to output another energy to the first heat pump element 13A. The control unit 15A, electrically connected with the temperature sensor 12, the first driver element 151 and the second driver element 152, is to evaluate the sensing result of the temperature sensor 12 to control an energy output to the first driver element 151 and also determine another energy output in accordance with the temperature-energy relationship to the second driver element 152. Thereupon, the first thermal energy of the heating element 11 and the first temperature difference of the first heat pump element 13A can be controlled.

For example, as shown in FIG. 1B, in the case that the temperature of the first heating block 14A is 57° C., and that of the second heating block 14B is 95° C., then the temperature difference between the first surface 131 and the second surface 132 of the first heat pump element 13A would be 95° C.−57° C.=38° C. Thus, the temperature sensor 12 would detect the real-time temperature of the heating element 11 via the first heating block 14A. The sensing result would be sent back to the control unit 15A as a reference for the first driver element 151 to determine the output energy for the heating element 11 to control the temperature at 57° C. At the same time, the control unit 15A would utilize the temperature-energy relationship of the first heat pump element 13A to determine the required energy (For example, as shown in FIG. 1C, the required energy for the 38° C. temperature difference would fall within 1~1.5V), and the second driver element 152 is utilized to generate a corresponding output energy to the first heat pump element 13A so as to control the temperature difference at 38° C.

Figure 1D:
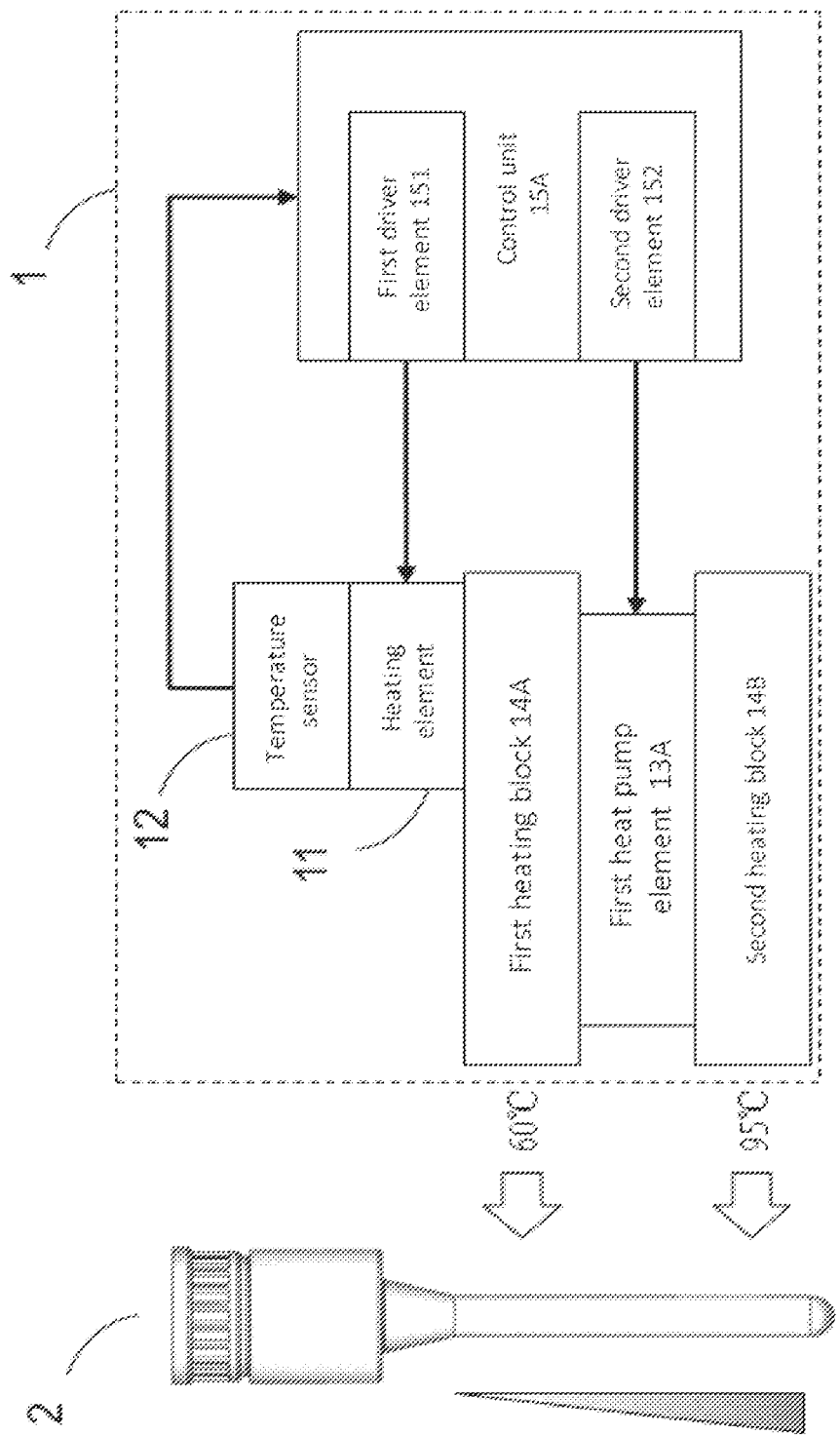
FIG. 1D is a schematic view of another exemplary example of the embodiment of FIG. 1B.

Referring to FIG. 1D, FIG. 1D is a schematic view of another exemplary example of the embodiment of FIG. 1B. In this embodiment, the first heat pump element 13A, the first heating block 14A and the second heating block 14B of the heating device for a convective polymerase chain reaction 1 are structurally and functionally the same to those of FIG. 1B, and thus details thereabout would be omitted herein. However, in FIG. 1D, the first driver element 151 and the second driver element 152 are integrated into the control unit 15A, so that the component quantity can be reduced, the volume of the heating device can be smaller, and the production cost can be down. In addition, the temperature sensor 12 of this embodiment is disposed on the heating element 11 or integrated with the heating element 11 as a unit piece, such that the temperature sensor 12 can contact directly with the heating element 11. As such, the temperature sensor 12 can evaluate directly the first thermal energy of the heating element 11. The sensing result can be sent back to the control unit 15A of the controller 15 for necessary calculation. Then, the output energy for the heating element 11 can be determined.

Figure 2A:
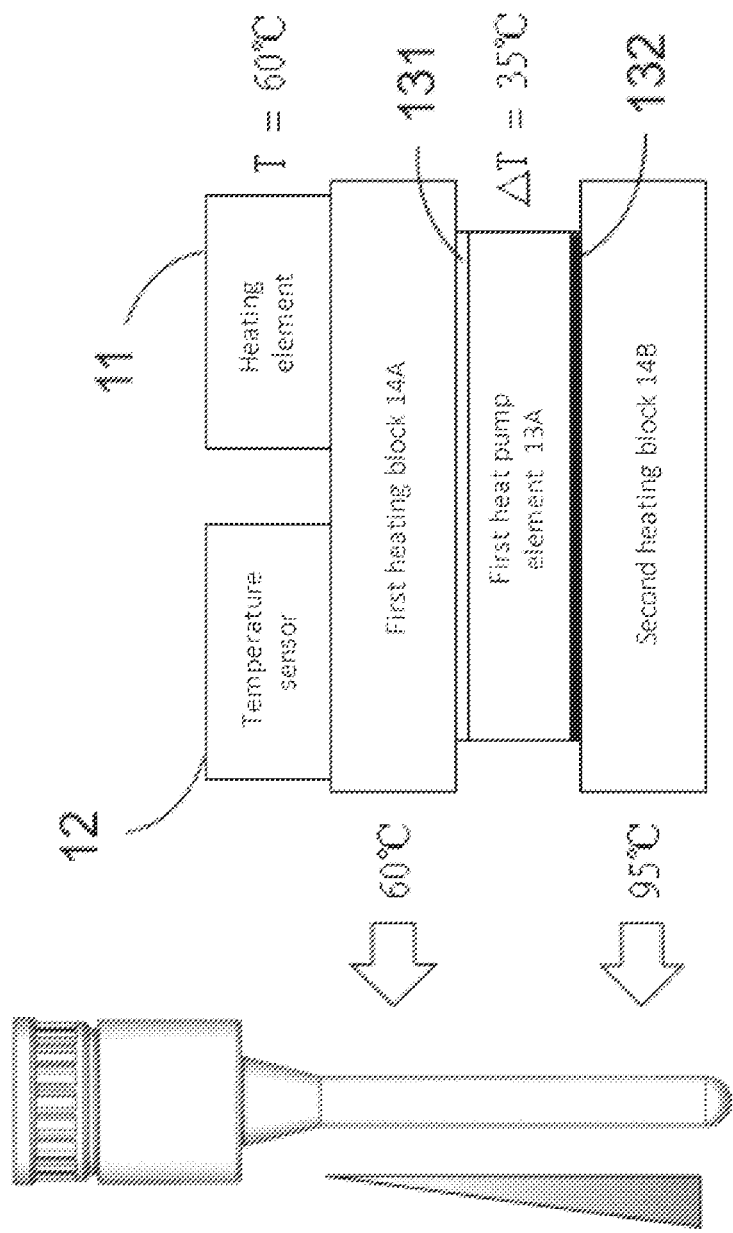
FIG. 2A shows schematically a portion of FIG. 1B, in a manner of highlighting the cold and hot surfaces of the heating device of this disclosure.

Referring to FIG. 2A, a portion of FIG. 1B, in a manner of highlighting the cold and hot surfaces of the heating device of this disclosure, is shown schematically. In this embodiment, the first surface 131 of the first heat pump element 13A is a cold surface, and the second surface 132 thereof is a hot surface. For example, as shown, the first thermal energy temperature of the heating element 11 is 60° C., and the cold surface temperature of the first heat pump element 13A is also 60° C. Since the hot surface temperature of the first heat pump element 13A is higher than the cold surface temperature thereof, and the temperature difference is 35° C., thus the second thermal energy temperature for the hot surface would be 60° C.+35° C.=95° C. In addition, since the second heating block 14B is contacted with the hot surface of the first heat pump element 13A, thus the temperature of the second heating block 14B is also equal to 95° C.

Figure 2B:
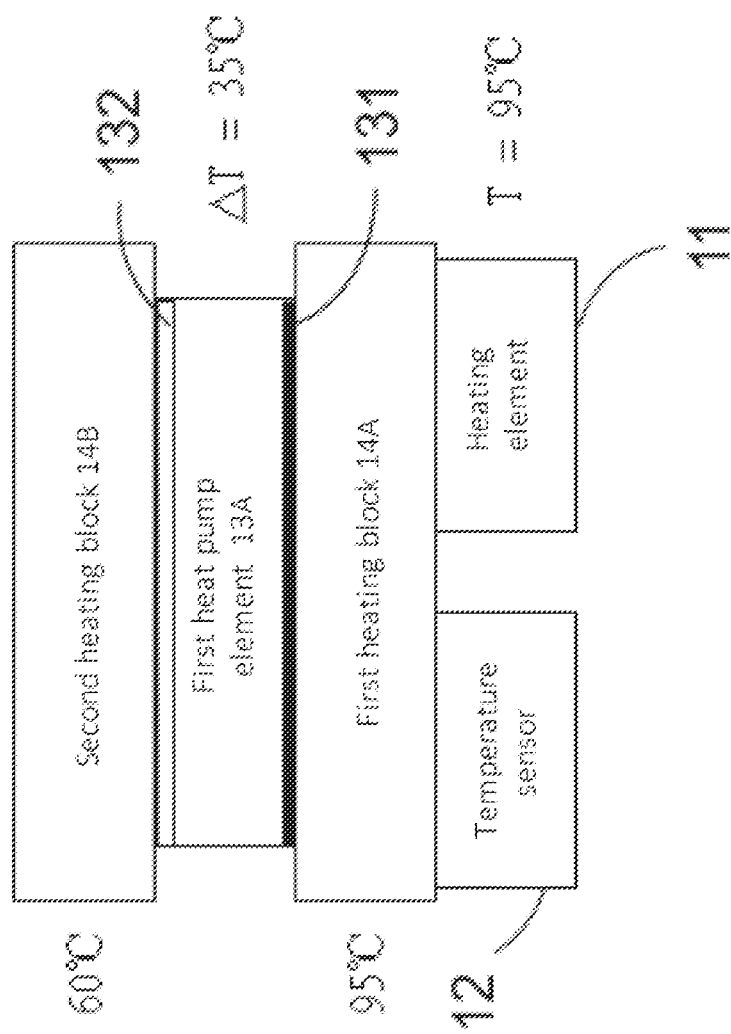
FIG. 2B is a schematic view of another exemplary example of the embodiment of FIG. 2A.

Referring to FIG. 2B, another exemplary example of the embodiment of FIG. 2A is schematically shown. The major difference between FIG. 2B and FIG. 2A is that, in this embodiment, the first surface 131 of the first heat pump element 13A is a hot surface, and the second surface 132 thereof is a cold surface. That is, the cold and hot surfaces of the first heat pump element 13A are switched to each other, or the energy polarities outputted to the first heat pump element 13A is varied. For example, the polarities of the voltages or currents are reverse to each other, but not limited thereto. Hence, if the heating element 11 is to generate a first thermal energy temperature of 95° C., then, since the hot surface temperature of the first heat pump element 13A is higher than the cold surface temperature thereof and the temperature difference is 35° C., the second thermal energy temperature of the cold surface would be 95° C.−35° C.=60° C. In addition, since the second heating block 14B is contacted with the cold surface of the first heat pump element 13A, thus the temperature of the second heating block 14B is also equal to 60° C.

Figure 3A:
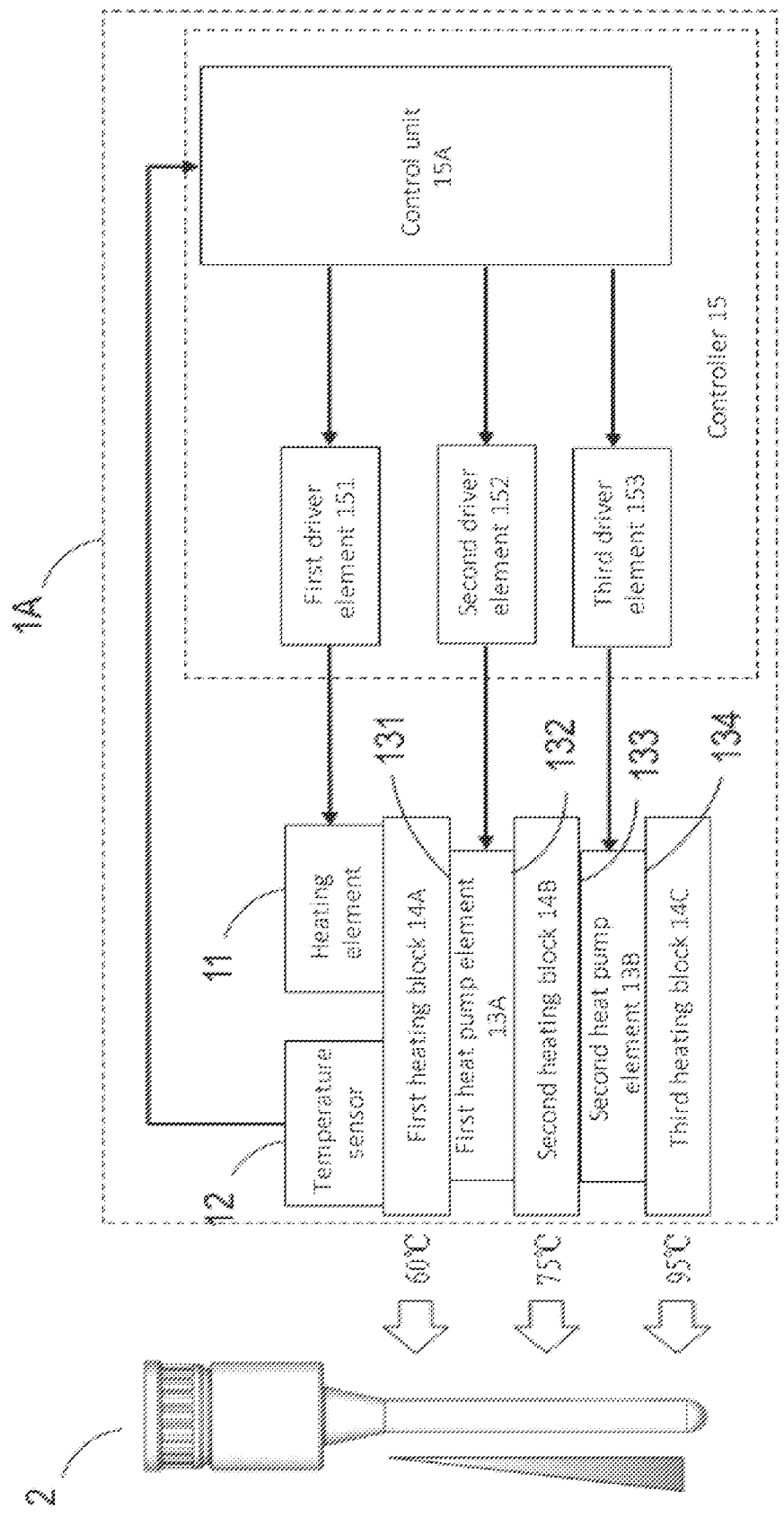
FIG. 3A is a schematic view of a second embodiment of the heating device for a convective polymerase chain reaction in accordance with this disclosure.

Referring to FIG. 3A, a schematic view of a second embodiment of the heating device for a convective polymerase chain reaction in accordance with this disclosure is shown. In this embodiment, since the heating element 11, the temperature sensor 12, the first heat pump element 13A, the first heating block 14A and the second heating block 14B of the heating device for a convective polymerase chain reaction 1A are all structurally and functionally resembled to those of FIG. 1B, thus details thereabout are omitted herein. However, in FIG. 3A, the heating device for a convective polymerase chain reaction 1A further includes a second heat pump element 13B and a third heating block 14C. The second heat pump element 13B, having a third surface 133 and a fourth surface 134, is configured to receive an energy from the controller 15 so as to generate a second temperature difference between the third surface 133 and the fourth surface 134. In this embodiment, the energy required by the second temperature difference is obtained from realizing the temperature-energy relationship (FIG. 1C, for example). In addition, the second heating block 14B is contacted with the third surface 133 of the second heat pump element 13B. The second heating block 14B would transfer the received second thermal energy to the second heat pump element 13B, so that the second heat pump element 13B can use the second thermal energy and the second temperature difference to generate a third thermal energy.

The third heating block 14C, contacted with the fourth surface 134 of the second heat pump element 13B, is configured to receive the third thermal energy of the second heat pump element 13B. Similarly, the third heating block 14C is made of a low thermal resistance material, such as aluminum, copper, ceramic, etc.; but not limited thereto.

In this embodiment, the second heat pump element 13B is disposed between the second heating block 14B and the third heating block 14C. In addition, the controller 15 further includes a third driver element 153 electrically connected with the second heat pump element 13B. The third driver element 15 is configured to output an energy to the second heat pump element 13B, such that the second temperature difference of the second heat pump element 13B can be controlled.

For example, as shown in FIG. 3A, in the case that the temperature of the first heating block 14A is 60° C., that of the second heating block 14B is 75° C., and that of the third heating block 14C is 95° C., then the temperature difference between the first surface 131 and the second surface 132 of the first heat pump element 13A would be 75° C.−60° C.=15° C., and the temperature difference between the third surface 133 and the fourth surface 134 of the second heat pump element 13B would be 95° C.−75° C.=20° C. Then, the temperature sensor 12 would detect the real-time temperature of the heating element 11 via the first heating block 14A. The sensing result would be sent back to the control unit 15A as a reference for the first driver element 151 to determine the output energy for the heating element 11 to control the temperature at 60° C. At the same time, the control unit 15A would utilize the temperature-energy relationships of the first heat pump element 13A and the second heat pump element 13B to determine the required energy intensity (For example, as shown in FIG. 1C, the required energy for the 15° C. temperature difference would fall within 0.25~0.75V, and the required energy for the 20° C. temperature difference would fall within 0.5~1.0V), and the second driver element 152 and the third driver element 153 are utilized to generate corresponding output energies to the first heat pump element 13A and the second heat pump element 13B so as to control the temperature differences at 15° C. and 20° C., respectively.

Figure 3B:
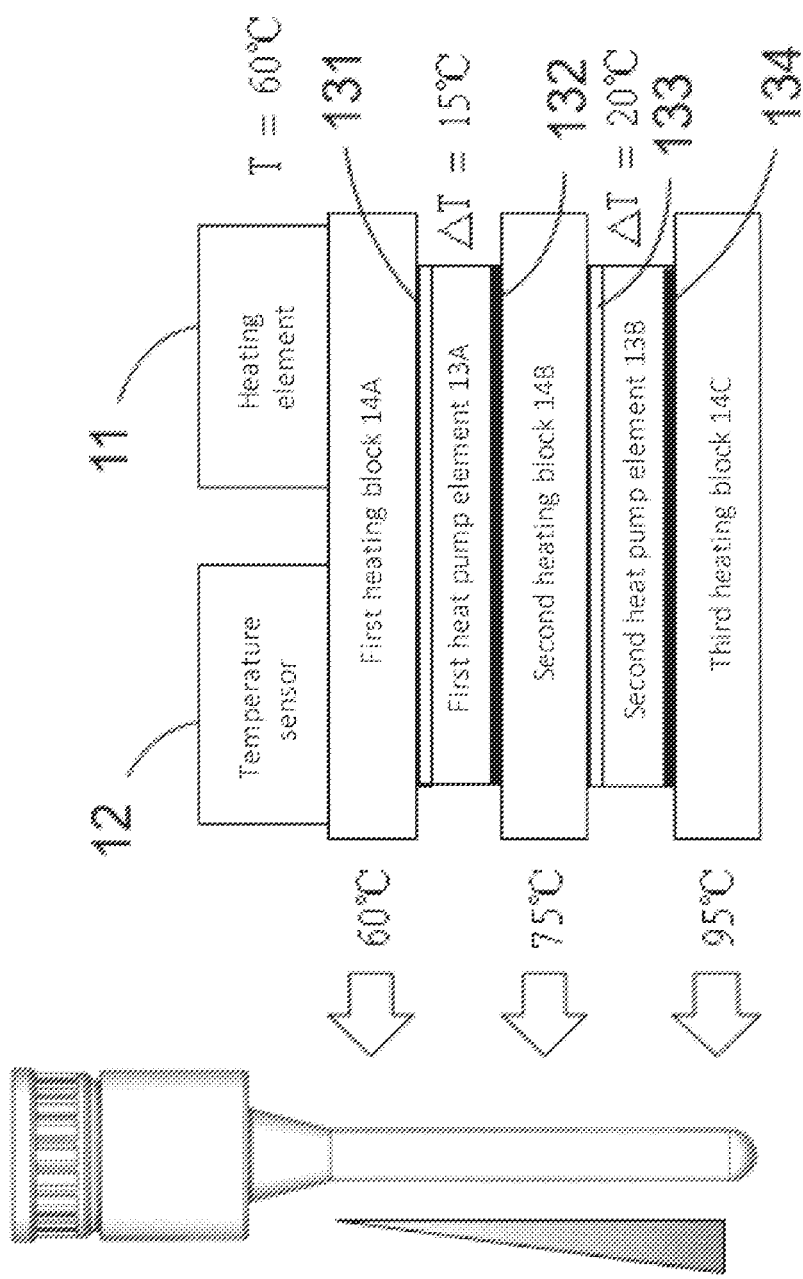
FIG. 3B shows schematically a portion of FIG. 3A, in a manner of highlighting the cold and hot surfaces of the heating device of this disclosure.

Referring to FIG. 3B, a portion of FIG. 3A is schematically shown, in a manner of highlighting the cold and hot surfaces of the heating device of this disclosure. In this embodiment, the first surface 131 of the first heat pump element 13A is a cold surface, the second surface 132 of the first heat pump element 13A is a hot surface, the third surface 133 of the second heat pump element 13B is a cold surface, and the fourth surface 134 of the second heat pump element 13B is a hot surface. For example, as shown, the first thermal energy temperature of the heating element 11 is 60° C., and the temperature of the first surface 131 of the first heat pump element 13A is also 60° C. Since the temperature of the second surface 132 of the first heat pump element 13A is higher than the temperature of the first surface 131 thereof, and the temperature difference is 15° C., thus the temperature of the second surface 132 would be 60° C.+15° C.=75° C. In addition, since the second heating block 14B is contacted with both the second surface 132 of the first heat pump element 13A and the third surface 133 of the second heat pump element 13B, thus the temperature of the second heating block 14B is also equal to 75° C. Furthermore, since the temperature of the fourth surface 134 of the second heat pump element 13B is higher than the temperature of the third surface 133 thereof, and the temperature difference is 20° C., thus the temperature of the fourth surface 134 would be 75° C.+20° C.=95° C. In addition, since the third heating block 14C is contacted with the fourth surface 134 of the second heat pump element 13B, thus the temperature of the third heating block 14C is also equal to 95° C.

Figure 3C:
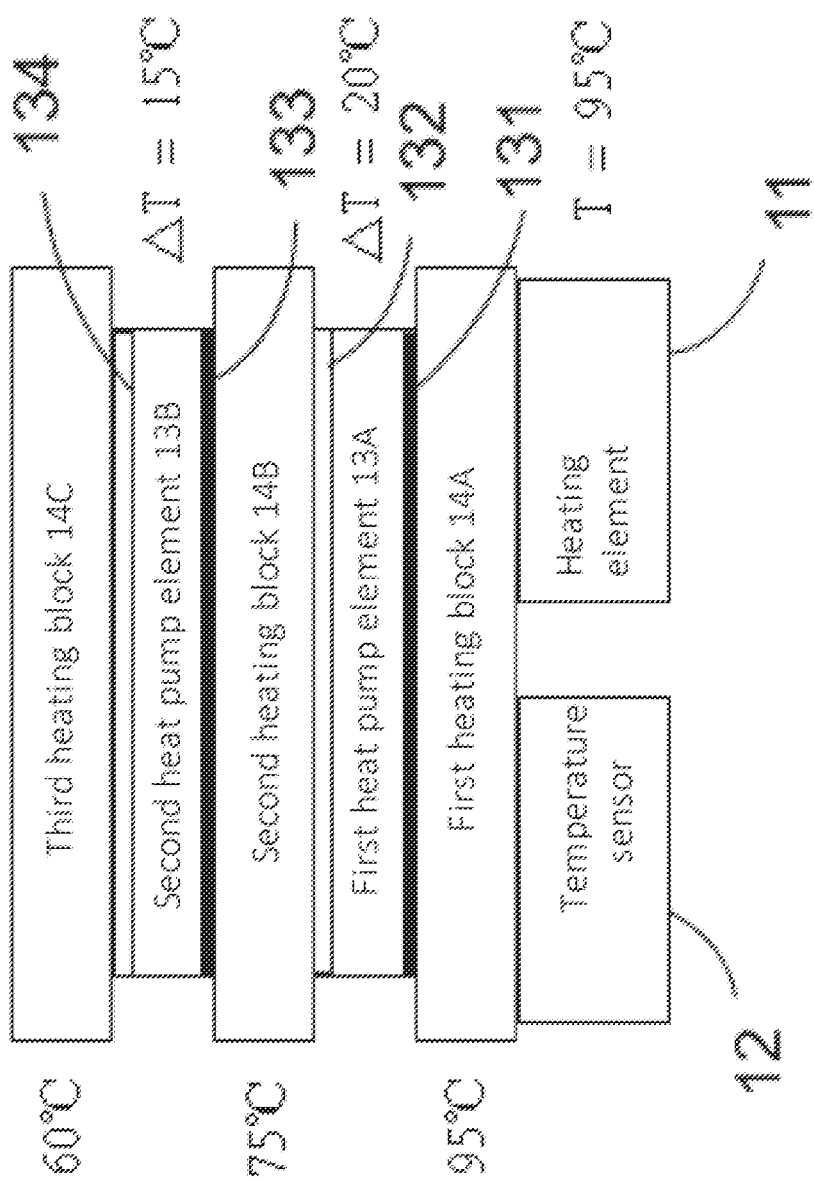
FIG. 3C is a schematic view of another exemplary example of the embodiment of FIG. 3B.

Referring to FIG. 3C, FIG. 3C is a schematic view of another exemplary example of the embodiment of FIG. 3B. With the structuring shown in FIG. 3C, the temperature arrangement in FIG. 3B can be also achieved. The major difference between FIG. 3C and FIG. 3B is that, in this embodiment, the first surface 131 of the first heat pump element 13A is a hot surface, the second surface 132 of the first heat pump element 13A is a cold surface, the third surface 133 of the second heat pump element 13B is a hot surface, and the fourth surface 134 of the second heat pump element 13B is a cold surface. That is, the cold and hot surfaces of either the first heat pump element 13A or the second heat pump element 13B are switched to each other, or the energy polarities outputted to the first heat pump element 13A and the second heat pump element 13B are changed. For example, the polarities of the voltages or currents are reverse, but not limited thereto. Thus, if the first thermal energy temperature of the heating element 11 is 95° C., since the temperature of the cold surface of the first heat pump element 13A is lower than the temperature of the hot surface thereof by 20° C., thus the second thermal energy temperature of the cold surface would be 95° C.−20° C.=75° C. In addition, since the second heating block 14B is contacted with both the cold surface of the first heat pump element 13A and the hot surface of the second heat pump element 13B, thus the temperature of the second heating block 14B is also equal to 75° C. Furthermore, since the temperature of the cold surface of the second heat pump element 13B is lower than the temperature of the hot surface thereof by 15° C., thus the third thermal energy temperature of the cold surface would be 75° C.−15° C.=60° C. In addition, since the third heating block 14C is contacted with the cold surface of the second heat pump element 13B, thus the temperature of the third heating block 14C is also equal to 60° C.

From FIG. 1B and FIG. 3A, it is understood that a correspondence relationship exists between the quantity of the heat pump elements and the quantity of the heating blocks. For example, if the quantity of the first heat pump element in FIG. 1B is 1, and the total quantity of the first heating block and the second heating block is 2, thus the relationship would be: Quantity (first heat pump element)=Quantity (first heating block+second heating block)−1. Referring to FIG. 3A, the total quantity of the first heat pump element and the second heat pump element is 2, and that of the first heating block, the second heating block and the third heating block is 3, thus the relationship would be: Quantity (first heat pump element+second heat pump element)=Quantity (first heating block+second heating block+third heating block)−1. Namely, according to this disclosure, a relationship exists between the quantity M of the heat pump elements and the quantity N of the heating blocks: i.e., M=N−1. That is, in this disclosure, the total quantity of the heat pump elements is less than that of the heating blocks by 1.

Figure 4A:
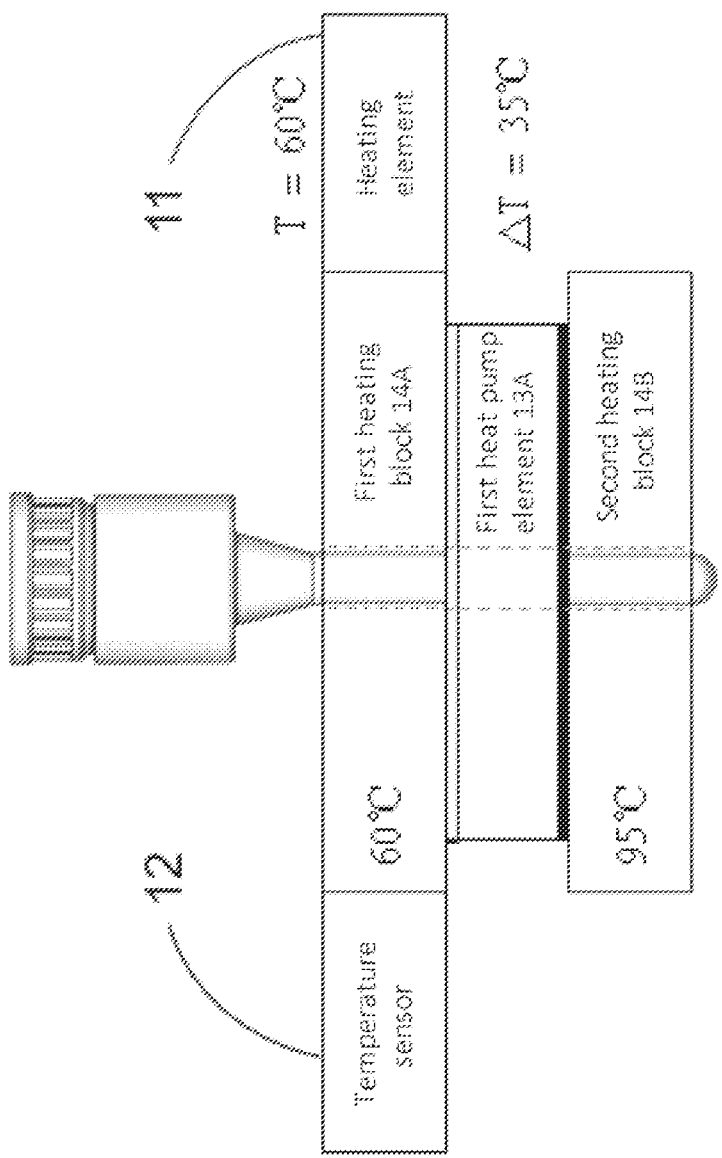
FIG. 4A is a schematic view of a third embodiment of the heating device for a convective polymerase chain reaction in accordance with this disclosure.

Referring to FIG. 4A, a schematic view of a third embodiment of the heating device for a convective polymerase chain reaction in accordance with this disclosure is shown. In this embodiment, the first heat pump element 13A, the first heating block 14A and the second heating block 14B are structurally and functionally resembled to those of FIG. 1B, and thus details thereabout would be omitted herein. However, in FIG. 4A, the heating element 11 is disposed at a side of the first heating block 14A while the temperature sensor 12 is disposed at another side thereof. Functions of the heating element 11 and the temperature sensor 12 in this embodiment are also resembled to those in FIG. 1B, and thus details thereabout would be omitted herein. In this embodiment, each of the first heat pump element 13A, the first heating block 14A and the second heating block 14B is furnished with a through hole for receiving the container (i.e., the bio-reactor); preferably, in a contact manner. As such, the entire occupation of the device can be reduced, without sacrificing the temperature gradient and the heat convection for the nucleic acid amplification inside the container 2. For example, if the through holes of the first heating block 14A, the first heat pump element 13A and the second heating block 14B are coaxial, then the extension pipe of the container 2 can be introduced to penetrate through these through holes for performing the heat convection.

Figure 4B:
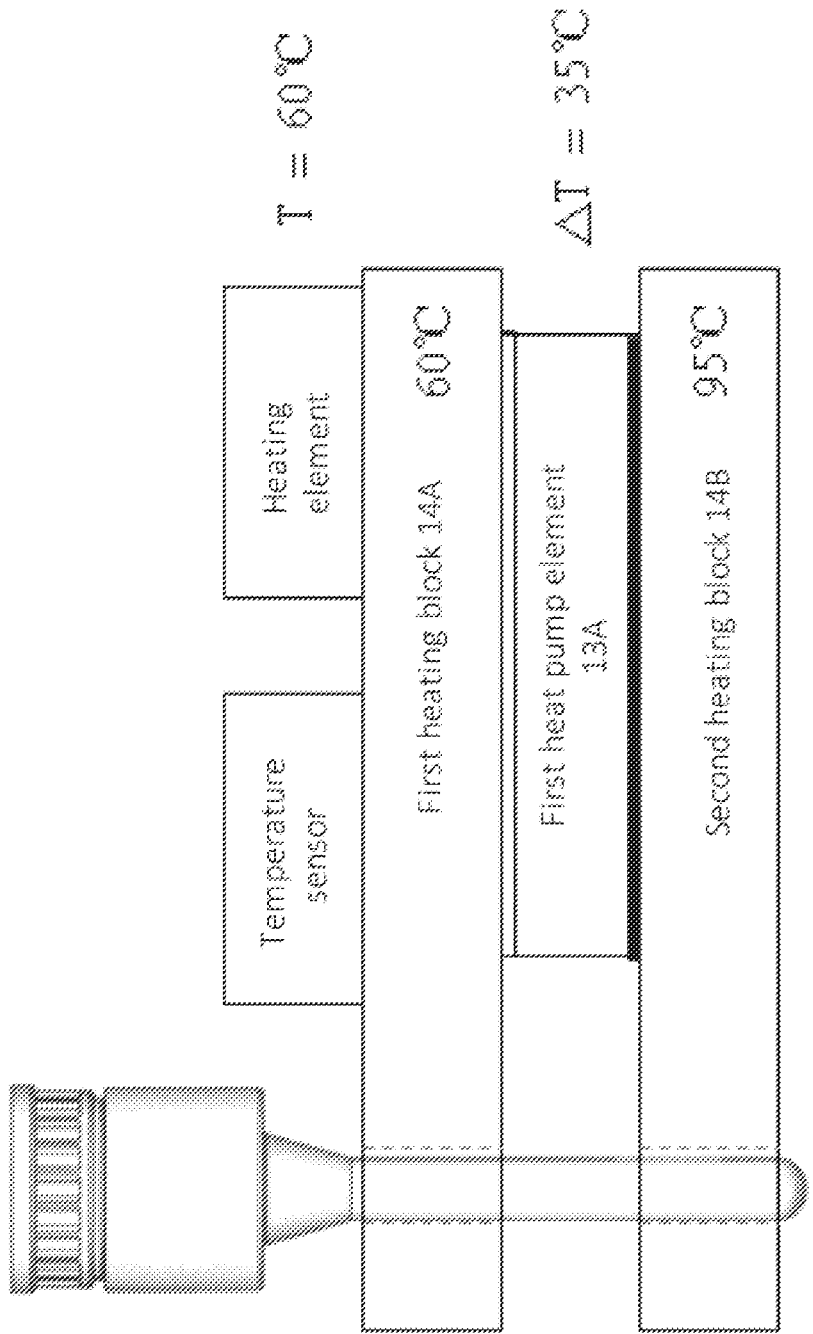
FIG. 4B is a schematic view of another exemplary example of the embodiment of FIG. 4A.
Figure 4C:
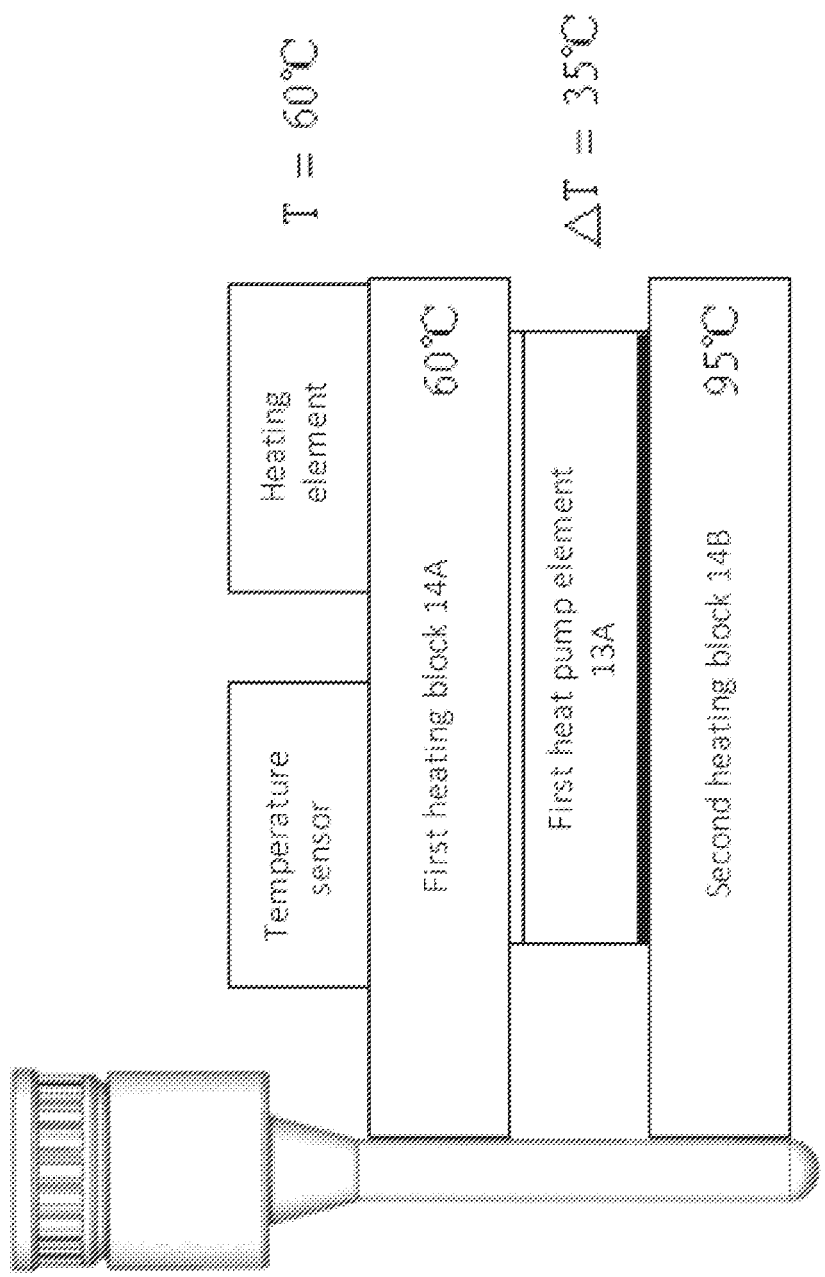
FIG. 4C is a schematic view of a further exemplary example of the embodiment of FIG. 4A.

Refer to FIG. 4B and FIG. 4C; where FIG. 4B is a schematic view of another exemplary example of the embodiment of FIG. 4A, and FIG. 4C is a schematic view of a further exemplary example of the embodiment of FIG. 4A. In these examples, the heating elements 11, the temperature sensors 12, the first heat pump element 13A, the first heating blocks 14A, and the second heating blocks 14B are structurally and functionally resembled to those of FIG. 1B and thus details thereabout would be omitted herein. However, in FIG. 4B, only the through holes of the first heating block 14A and the second heating block 14B are coaxial to receive and also contact the container 2. Under such an arrangement, in comparison with FIG. 4A, since no through hole is needed at the first heat pump element 13A, thus the production cost would be lower, without sacrificing the temperature gradient and the heat convection for the nucleic acid amplification inside the container 2. On the other hand, in FIG. 4C, sides of the first heating block 14A and the second heating block 14B are directly contacted with the container 2, thus similar temperature gradient and heat convection can be formed to perform the nucleic acid amplification.

Figure 4D:
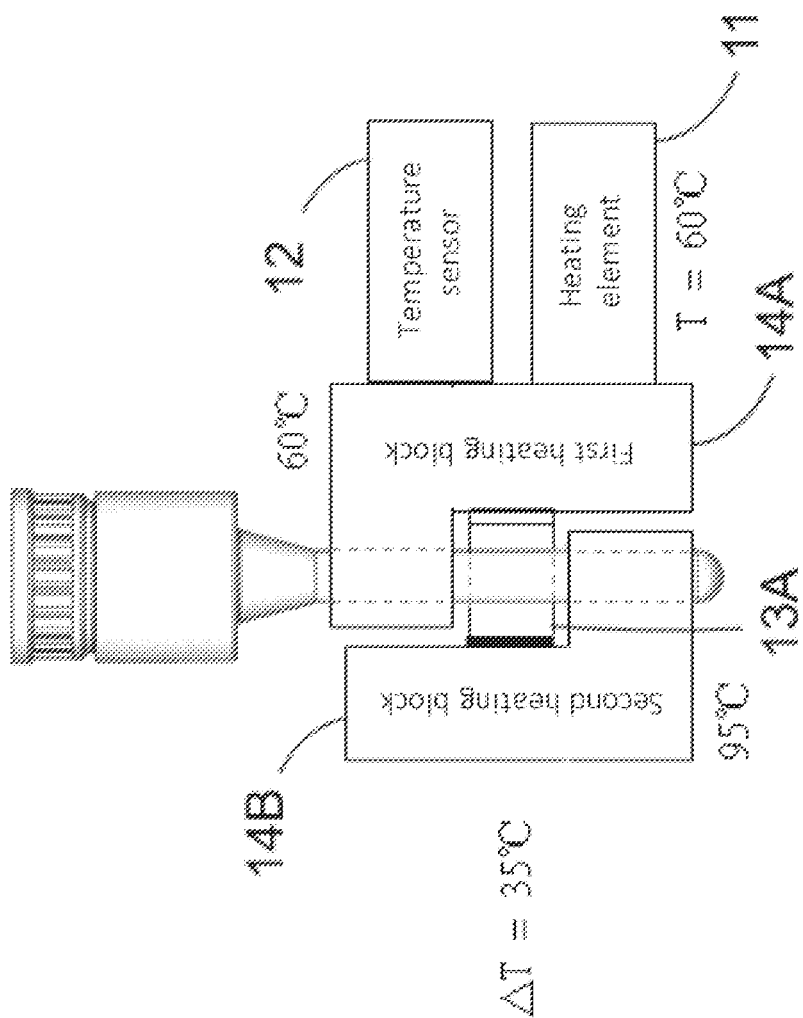
FIG. 4D is a schematic view of one more exemplary example of the embodiment of FIG. 4A, with geometric shapes of heating blocks.
Figure 4E:
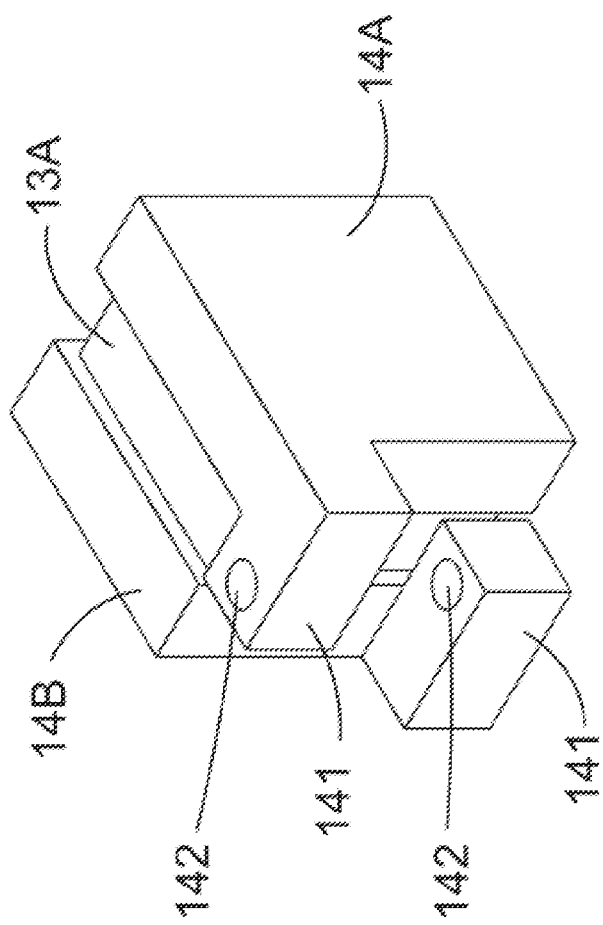
FIG. 4E is an isometric view of the geometric shapes of heating blocks of FIG. 4D.

Refer to FIG. 4D and FIG. 4E; where FIG. 4D is a schematic view of one more exemplary example of the embodiment of FIG. 4A with geometric shapes of heating blocks, and FIG. 4E is an isometric view of the geometric shapes of heating blocks of FIG. 4D. In this embodiment, the first heating block 14A and the second heating block 14B are both machining structures. The first heating block 14A has an extension portion 141, the second heating block 14B has another extension portion 141, and both the extension portions 141 are furnished with individual through holes 142. However, the first heat pump element 13A is provided without a through hole. The first heat pump element 13A is adjacent to the container 2 without the extension pipe thereof to penetrate through the first heat pump element 13A. It shall be noted and understood that the L-shape configurations of the first heating block 14A and the second heating block 14B shown in this embodiment are simply examples from various embodiments, not particularly limited thereto. In addition, a vertical arrangement had been applied to the first heat pump element 13A of this embodiment, different to the horizontal arrangement shown in FIG. 4A, FIG. 4B and FIG. 4C. With this vertical arrangement, in comparison with the aforesaid horizontal arrangement, the entire occupation of the device can be further reduced. Further, since the first heat pump element 13A is provided with no through hole, thus the production cost would be lower. In FIG. 4D, similar temperature gradient and heat convection can be formed to perform the nucleic acid amplification inside the container 2.

Figure 5A:
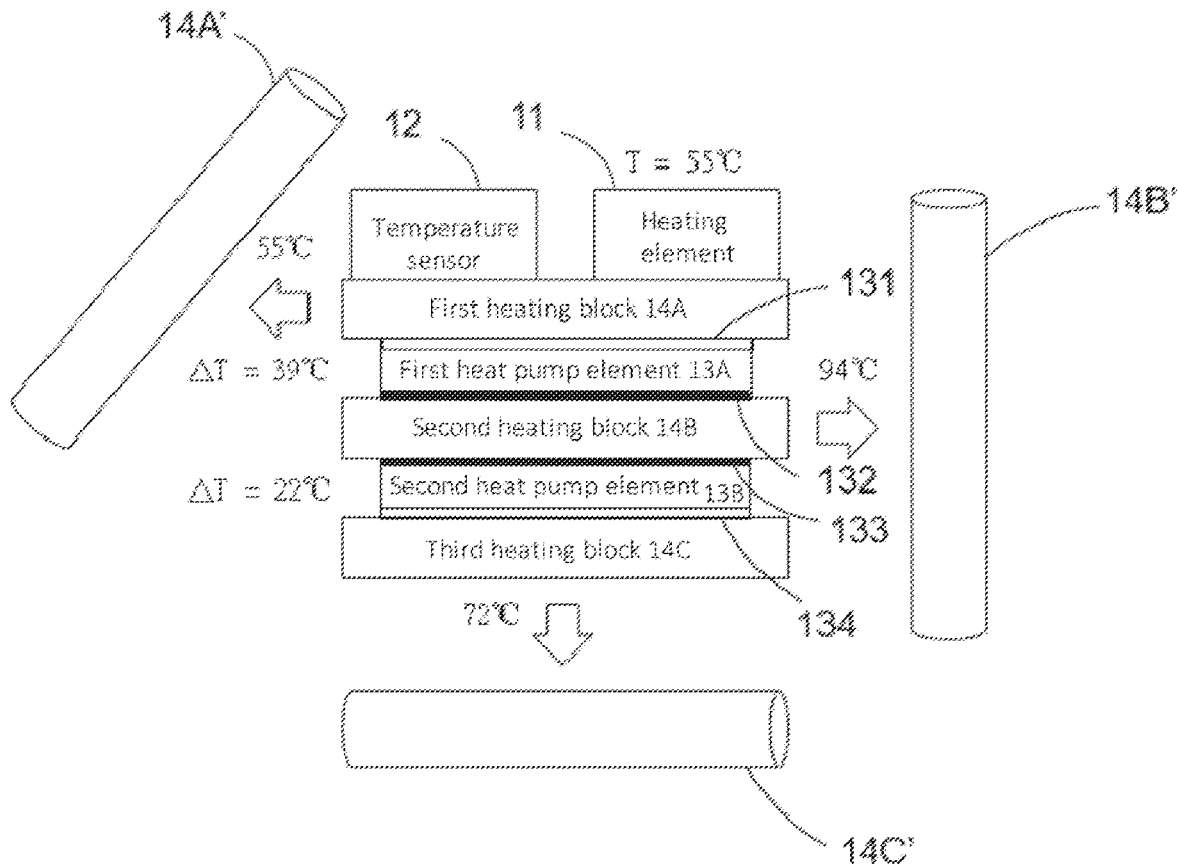
FIG. 5A is a schematic view of a fourth embodiment of the heating device for a convective polymerase chain reaction in accordance with this disclosure.

Referring to FIG. 5A, a schematic view of a fourth embodiment of the heating device for a convective polymerase chain reaction in accordance with this disclosure is shown. It is noted that FIG. 5A is simply another variation of FIG. 3B. A difference between FIG. 5A and FIG. 3B is that the cold and hot surfaces of the second heat pump element 13B are switched to each other, or the energy polarities outputted to the second heat pump element 13B are exchanged. For example, the polarities of the voltages or currents are reverse, but not limited thereto. Thus, in the case that the first thermal energy temperature generated by the heating element 11 is 55° C., then, since the temperature of the second surface 132 (hot surface) of the first heat pump element 13A is higher than that of the first surface 131 (cold surface) thereof by a temperature difference of 39° C., the second thermal energy of the hot surface would be 55° C.+39° C.=94° C. Further, since the second heating block 14B is contacted with both the hot surface of the first heat pump element 13A and the hot surface of the second heat pump element 13B, thus the temperature of the second heating block 14B would be also the 94° C. Furthermore, since the temperature of the fourth surface 134 (cold surface) of the second heat pump element 13B is lower than that of the third surface 133 (hot surface) thereof by a temperature difference of 22° C., thus the third thermal energy temperature of the cold surface would be 94° C.−22° C.=72° C. In addition, since the third heating block 14C is contacted with the cold surface of the second heat pump element 13B, thus the temperature of the third heating block 14C would be also the 72° C.

Figure 5B:
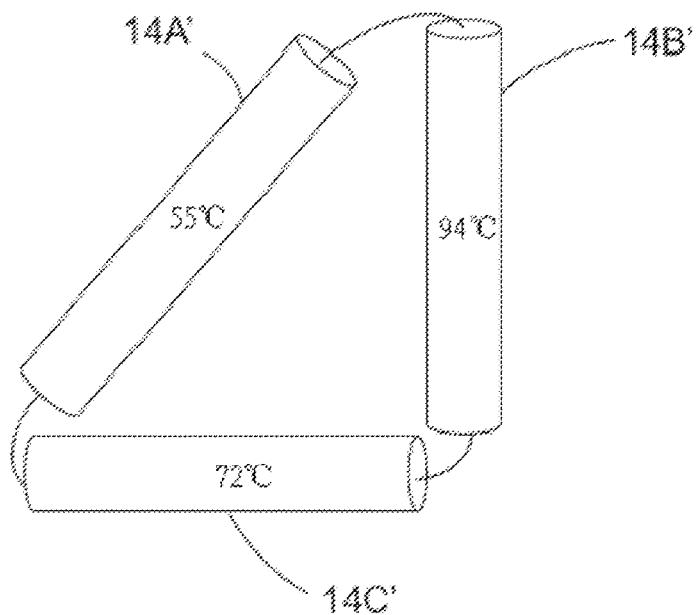
FIG. 5B is a schematic view of the arrangement of heating blocks which is another exemplary example of the embodiment of FIG. 5A.
Figure 5C:
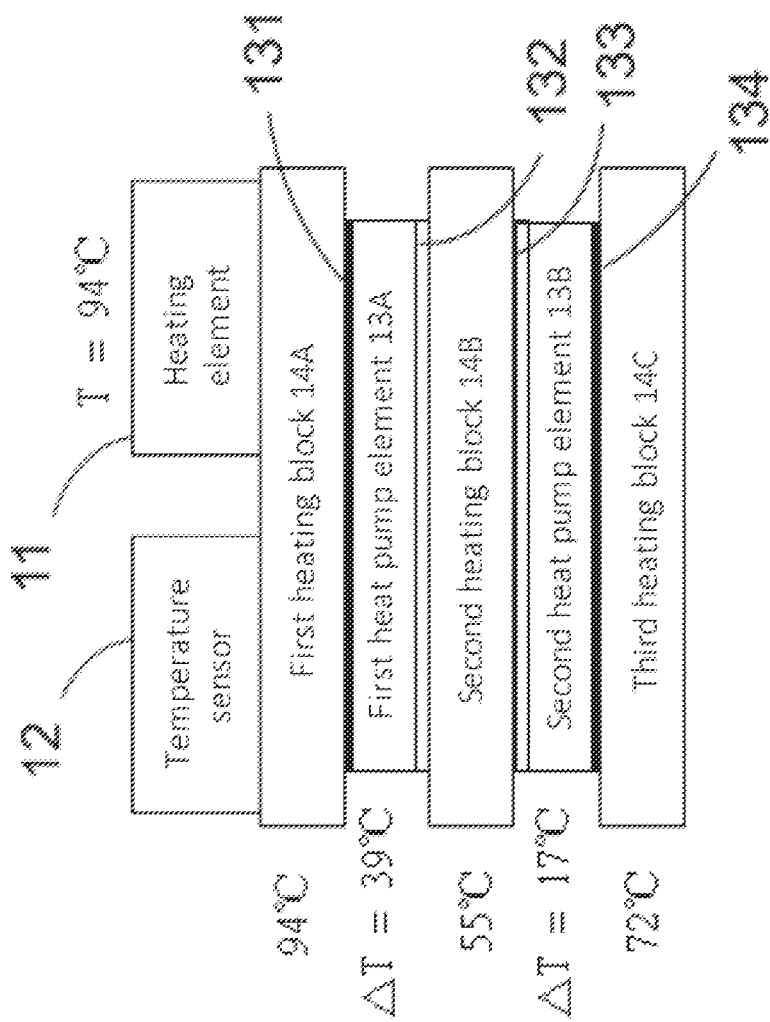
FIG. 5C is a schematic view of another exemplary example of the embodiment of FIG. 5A.

In the example of FIG. 5A, the first heating block 14A can be disposed to contact the first heating rod 14A', the second heating block 14B can be disposed to contact the second heating rod 14B', and the third heating block 14C can be disposed to contact the third heating rod 14C'. Further, the first heating rod 14A', the second heating rod 14B' and the third heating rod 14C' can be arranged into a module applicable to the closed-loop reactor so as to induce the heat convection for promoting the nucleic acid amplification, as shown in FIG. 5B Referring to FIG. 5C, a schematic view of another exemplary example of the embodiment of FIG. 5A is shown. A difference between FIG. 5C and FIG. 5A is that the cold and hot surfaces of each of the first and second heat pump elements 13A, 13B are switched to each other, or the energy polarities outputted to the first and second heat pump elements 13A, 13B are exchanged. For example, in the case that the first thermal energy temperature generated by the heating element 11 is 94° C., then, since the temperature of the second surface 132 (cold surface) of the first heat pump element 13A is lower than that of the first surface 131 (hot surface) thereof by a temperature difference of 39° C., the second thermal energy temperature of the cold surface would be 94° C.−39° C.=55° C. Further, since the second heating block 14B is contacted with both the cold surface of the first heat pump element 13A and the cold surface of the second heat pump element 13B, thus the temperature of the second heating block 14B would be also the 55° C. Furthermore, since the temperature of the fourth surface 134

(hot surface) of the second heat pump element 13B is higher than that of the third surface 133 (cold surface) thereof by a temperature difference of 17° C., thus the temperature of the hot surface would be 55° C.+17° C.=72° C. In addition, since the third heating block 14C is contacted with the hot surface of the second heat pump element 13B, thus the temperature of the third heating block 14C would be also the 72° C.

Figure 6:
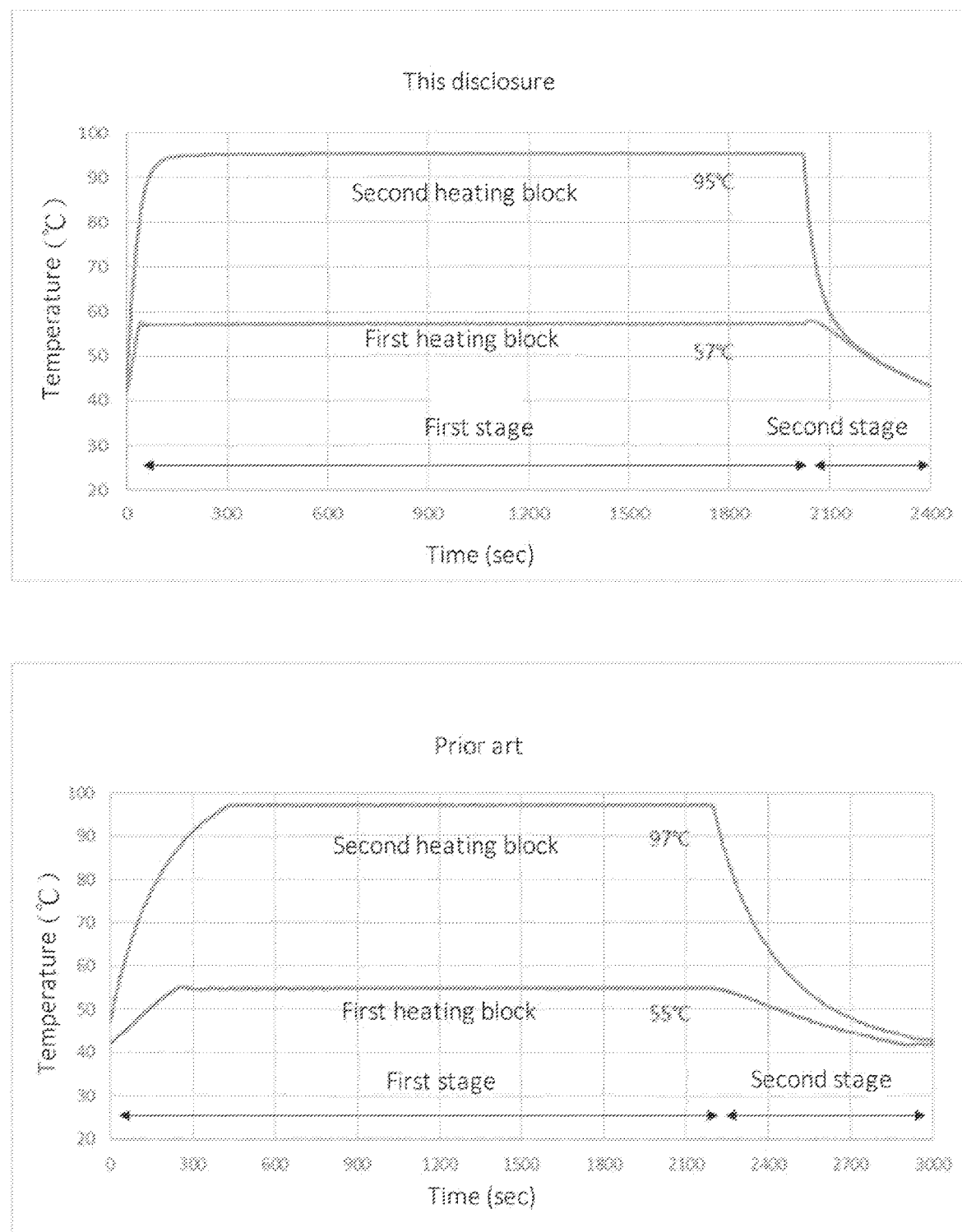
FIG. 6 demonstrates schematically oscillograms of temperature variations at the heating blocks for this disclosure and a conventional design.

Referring to FIG. 6, schematic oscillograms of temperature variations at the heating blocks for this disclosure and a conventional design are demonstrated. In the aforesaid description of this disclosure, the embodiment of FIG. 1B is applied to form the oscillogram of the variations of the heating block temperature. In the following description, temperature variations at the first heating block 14A and the second heating block 14B would be explained, while the heating device for a convective polymerase chain reaction 1 is operated. Since 57° C. and 95° C. are required for inducing heat circulation for promoting the nucleic acid amplification, thus the first thermal energy temperature of the heating element 11 is set to be 57° C., and the first temperature difference of the first heat pump element 13A is set to be 38° C. (95° C.−57° C.=38° C.). As such, the temperature of the first heating block 14A would be the same 57° C. as the first thermal energy temperature of the heating element 11, and the temperature of the second heating block 14B would be the same 95° C. as the second thermal energy temperature generated by the first heat pump element 13A. As shown, when the heating device for a convective polymerase chain reaction 1 is operated, temperatures of the heating block 14A and the second heating block 14B would rise rapidly. After the temperature of the first heating block 14A reaches 57° C., then the temperature would become stable. On the other hand, to the second heating block 14B, the temperature would be stable after reaching 95° C. At this time, the high temperature of the second heating block 14B would be limited by the heat pump effect of the first heat pump element 13A, by which the heat transfer from the first heat pump element 13A to the first heating block 14A would be stopped, as shown in the first stage. On the other hand, when the heating device for a convective polymerase chain reaction 1 is stopped, since no heat pump effect exists, thus the high temperature of the second heating block 14B would be transmitted to the first heating block 14A, via the first heat pump element 13A, for a rapid heat dissipation, as shown in the second stage. Thus, according to this disclosure, in the case the heating device 1 is terminated, no additional heat-dissipation fin or fan is required, and so the entire volume and cost of the heating device can be substantially reduced.

In order to further demonstrate the advantage of this disclosure, an oscillogram obtained from a conventional design is used as a reference. Referring to FIG. 6, the temperature oscillogram of the conventional heating block as described in the background section conventional design after being modified by manufacturing the structural fixings of the two heating blocks (say, the first heating block and the second heating block) with a high thermal resistance material so as to reduce the possible interaction between the two heating blocks. However, the disadvantage of such a conventional design is that, when the heating device is stopped, since the high thermal resistance material exists for connections, it is obvious that, in the temperature drop in the second stage, the time required for heat dissipation would be longer due to the higher heat resistance, and so the heat-dissipation performance of the conventional design would be poorer than that of this disclosure. In addition, though the conventional design herein is already furnished with positive components such as fans, for enhancing the heat dissipation efficiency, yet the resulted heat-dissipation performance is still poorer than that of this disclosure. Beside, the conventional design is also less favorable due to its larger occupation and higher cost.

In summary, in the heating device for a convective polymerase chain reaction provided in this disclosure, the disclosed arrangements can resolve the heat conduction problems from a high temperature to a low temperature, of which, in the operation of the conventional heating element, a thermal disturbance would be induced while the thermal energy is transmitted from a high temperature zone to a low temperature zone. In addition, while the heating device of this disclosure is stopped, the thermal energy of the heating block with a higher temperature would be transmitted rapidly to another heating block with a lower temperature, such that the heat or temperature can be rapidly dissipated. Thereupon, no additional heat-dissipation component with a larger size, such as a heat-dissipation fin or fan, is required, and thus a miniaturization design is feasible. Further, since the largest temperature difference between the cold and hot surfaces of a general heat pump element is about 80° C., thus, if the aforesaid conventional design is long-term operated under an extreme condition of temperature difference, then, beside the mechanical stressing caused by thermal expansion, the energy efficiency of the heat pump element would become poorer if the temperature difference between the cold and hot surfaces of the heat pump element grows larger. Hence, with the structuring of the heating device in this disclosure, the required temperature difference between the cold and hot surfaces of the heat pump element would be lowered to one half of the aforesaid maximum temperature difference. Thereupon, except for the operating temperature difference is lowered, the service life of the heat pump element can be prolonged, and also the energy efficiency of the heat pump element can be much improved.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A heating device for a convective polymerase chain reaction, applied to form a temperature gradient and heat convection inside a container, said heating device comprising:
   a heating element, configured to receive energy and further transform the energy into a first thermal energy;
   a temperature sensor, configured to generate a sensing result according to the first thermal energy;
   a first heat pump element, having a first surface and a second surface, configured to receive energy and further generate a first temperature difference between the first surface and the second surface;
   a first heating block, contacted with the first surface of the first heat pump element and also the heating element, configured to receive the first thermal energy from the heating element and further transfer the first thermal energy to the first heat pump element, so as to have the first heat pump element to utilize the first thermal energy and the first temperature difference to generate a second thermal energy;

a second heating block, contacted with the second surface of the first heat pump element, configured to receive the second thermal energy of the first heat pump element; and a controller, electrically connected with the temperature sensor, the heating element and the first heat pump element, configured to output the energy in correspondence with the sensing result of the temperature sensor to the heating element and the first heat pump element, so as to control the first thermal energy of the heating element and the first temperature difference of the first heat pump element;

wherein the first heating block and the second heating block are simultaneously in contact with different portions of the container longitudinally;

wherein the controller controls energy outputted to the first heat pump in accordance with the first temperature difference of the first heat pump element and a temperature-energy relationship.

2. The heating device for a convective polymerase chain reaction of claim 1, wherein the temperature sensor is contacted with the first heating block, and according to the first thermal energy of the first heating block, the sensing result is sent back to the controller for calculation, so as to control energy outputted to the heating element.

3. The heating device for a convective polymerase chain reaction of claim 1, wherein the controller further includes:
a first driver element, electrically connected with the heating element, configured to output the energy to the heating element;
a second driver element, electrically connected with the first heat pump element, configured to output the energy to the first heat pump element; and
a control unit, electrically connected with the temperature sensor, the first driver element and the second driver element, configured to evaluate the sensing result of the temperature sensor to control the first driver element to output energy, and the temperature-energy relationship is used to control the second driver element to output energy, so as to control the first thermal energy of the heating element and the first temperature difference of the first heat pump element.

4. The heating device for a convective polymerase chain reaction of claim 3, wherein the first driver element and the second driver element are integrated into the control unit.

5. The heating device for a convective polymerase chain reaction of claim 1, wherein the temperature sensor is contacted with the heating element, and according to the first thermal energy of the heating element, the sensing result is sent back to the controller for calculation, so as to control the energy outputted to the heating element.

6. The heating device for a convective polymerase chain reaction of claim 1, wherein the first surface of the first heat pump element is a cold surface, and the second surface thereof is a hot surface.

7. The heating device for a convective polymerase chain reaction of claim 1, wherein the first surface of the first heat pump element is a hot surface, and the second surface thereof is a cold surface.

8. The heating device for a convective polymerase chain reaction of claim 1, wherein a quantity of the first heat pump element is M, a total quantity of the first heating block and the second heating block is N, and M=N−1.

9. The heating device for a convective polymerase chain reaction of claim 1, wherein the first heat pump element is a Peltier element.

10. The heating device for a convective polymerase chain reaction of claim 1, further including:
a second heat pump element, having a third surface and a fourth surface, configured to receive energy and further generate a second temperature difference between the third surface and the fourth surface, the second heating block being contacted with the third surface, wherein the second heating block receives the second thermal energy and further transfers the second thermal energy to the second heat pump element, and thus the second heat pump element generates a third thermal energy according to the second thermal energy and the second temperature difference; and
a third heating block, contacted with the fourth surface of the second heat pump element, configured to receive the third thermal energy of the second heat pump element;
wherein the controller controls the second temperature difference of the second heat pump element according to the temperature-energy relationship.

11. The heating device for a convective polymerase chain reaction of claim 10, wherein the second heat pump element is disposed between the second heating block and the third heating block.

12. The heating device for a convective polymerase chain reaction of claim 10, wherein the controller further includes a third driver element electrically connected with the second heat pump element for outputting a further energy to the second heat pump element so as to control the second temperature difference of the second heat pump element.

13. The heating device for a convective polymerase chain reaction of claim 10, wherein the third surface of the second heat pump element is a cold surface, and the fourth surface thereof is a hot surface.

14. The heating device for a convective polymerase chain reaction of claim 10, wherein the third surface of the second heat pump element is a hot surface, and the fourth surface thereof is a cold surface.

15. The heating device for a convective polymerase chain reaction of claim 1, wherein each of the first heating block and the second heating block is furnished with a through hole for allowing a portion of the container to penetrate therethrough in a contact manner, and thus the container is provided with the temperature gradient and the heat convection.

16. The heating device for a convective polymerase chain reaction of claim 1, wherein each of the first heat pump element, the first heating block and the second heating block is furnished with a through hole for allowing a portion of the container to penetrate therethrough, and the through hole of each of the first heating block and the second heating block is contacted with the portion of the container so as to provide the temperature gradient and the heat convection to the container.

* * * * *